United States Patent
Colli et al.

(10) Patent No.: US 8,748,476 B2
(45) Date of Patent: Jun. 10, 2014

(54) DARIFENACIN FOR USE IN THE TREATMENT OF URGENCY INDUCED BY OVERACTIVE BLADDER

(75) Inventors: Enrico Colli, Sandwich (GB); Paul Quinn, Sandwich (GB); Dzelal Serdarevic, Sandwich (GB); Larence Howard Skillern, Sandwich (GB)

(73) Assignee: Warner Chilcott Company, LLC, Fajardo, PR (US)

( * ) Notice: Subject to any disclaimer, the term of this patent is extended or adjusted under 35 U.S.C. 154(b) by 33 days.

(21) Appl. No.: 12/397,433

(22) Filed: Mar. 4, 2009

(65) Prior Publication Data
US 2009/0162433 A1 Jun. 25, 2009

Related U.S. Application Data

(63) Continuation of application No. 11/880,006, filed on Jul. 19, 2007, now abandoned, which is a continuation of application No. 10/256,420, filed on Sep. 26, 2002, now abandoned.

(60) Provisional application No. 60/347,456, filed on Jan. 11, 2002.

(51) Int. Cl.
*A61K 31/4025* (2006.01)
*A61K 9/10* (2006.01)
*A61K 31/40* (2006.01)

(52) U.S. Cl.
USPC ............ 514/422; 424/488; 514/966; 514/648

(58) Field of Classification Search
USPC ............................ 514/422, 966, 648; 424/488
See application file for complete search history.

(56) References Cited

U.S. PATENT DOCUMENTS 5,096,890 A 3/1992 Cross et al.
6,106,864 A 8/2000 Dolan et al.

FOREIGN PATENT DOCUMENTS

WO 97/09980 3/1997

OTHER PUBLICATIONS

Lemack, G., American Journal of Managed Care, "Overactive bladder: Optimizing quality of care", vol. 7, No. 2, pp. S46-S61, (2001).
J.N. Liberman et al., Elsevier Science Inc., Adult Urology 56 (6), pp. 1044-1050, "Health-Related Quality of Life Among Adults With Symptoms of Overactive Bladder: Results From a U.S. Community-Based Survey" (2001).
Pfizer Inc., Pfizer Voice, Issue 19, p. 9, "The Publication for All UK Staff", Oct. 2001.
C.R. Chapple, Elsevier Science Inc., Urology 55 (Supplement 5A). pp. 3-48. "Muscarinic Receptor Antagonists in the Treatment of Overactive Bladder", May 2000.
R.R. Dmochowski, et al., Elsevier Science Inc., Urology 56 (Supplement 6A), pp. 41-49, "Advancements in Pharmacologic Management of the Overactive Bladder", Dec. 2000.
V.A. Alabaster, Life Sciences, vol, 60, Nos. 13/14, pp. 1053-1060, "Discover & Development of Selective M3 Antagonists for Clinical Use" (1997).
Chancellor et al., "Tolterodine, an Effective and Well Tolerated Treatment for Urge Incontinence and Other Over Active Bladder Symptoms", Clin. Drug. Inves., vol. 19, No. 2, pp. 83-91 (2000).
Kobelt et al., "Quality-of-life Aspects of the Overactive Bladder and the Effect of Treatment with Tolterodine" BJU International, vol. 83, pp. 583-590 (1999).
Merck Manual 15th edition, p. 1639 (1987).

*Primary Examiner* — Savitha Rao
(74) *Attorney, Agent, or Firm* — Fitzpatrick, Cella, Harper & Scinto

(57) ABSTRACT

The invention provides the use of darifenacin, or a pharmaceutically acceptable derivative thereof, in the manufacture of a medicament for the reduction of urgency in patients suffering from overactive bladder.

5 Claims, No Drawings

DARIFENACIN FOR USE IN THE TREATMENT OF URGENCY INDUCED BY OVERACTIVE BLADDER

CROSS REFERENCE TO RELATED APPLICATION

This is a continuation of application Ser. No. 11/880,006, filed on Jul. 19, 2007, which is a continuation of application Ser. No. 10/256,420 filed on Sep. 26, 2002, which claims benefit of U.S. Provisional Application No. 60/347,456 filed Jan. 11, 2002, and U.K. Provisional Application No. 0129962.7 filed Dec. 14, 2001, the entire disclosures of which are hereby incorporated by reference.

This invention relates to a new use of darifenacin, and its pharmaceutically acceptable derivatives.

Darifenacin is (S)-2-(1-[2-(2,3-dihydrobenzofuran-5-yl)ethyl]-3-pyrrolidinyl)-2,2-diphenyl-acetamide and is disclosed in European Patent No 0388054, Examples 1B and 8. It is referred to therein as 3-(S)-(−)-(1-carbamoyl-1,1-diphenylmethyl)-1-[2-(2,3-dihydro-benzofuran-5-yl)ethyl]pyrroidine. It is indicated in the treatment of urinary incontinence and irritable bowel syndrome and has the following structure:

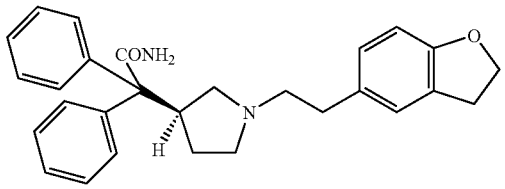 [SMILES: NC(=O)C(c1ccccc1)(c1ccccc1)[C@@H]1CCN(CCc2ccc3c(c2)CCO3)C1]

The symptoms of overactive bladder (OAB) include urinary frequency and urgency, with or without incontinence in the absence of local pathological or systemic condition. Urgency is described in the draft ICS Terminology Report [Terminology Report of the International Continence Society; Draft 6, 15 Aug. 2001] as the sudden compelling desire to pass urine, which is difficult to control.

Recently, the terms OAB Wet and OAB Dry have been proposed to describe OAB patients with or without incontinence respectively. Overall prevalence of OAB Wet and Dry is similar in men and women with a prevalence rate in the US of 16.6% [Stewart et al, Prevalence of Overactive Bladder in the United States: Results from the NOBLE Program; Abstract Presented at the $2^{nd}$ International Consultation on incontinence, July 2001, Paris, France]. Until recently, the cardinal symptom of OAB was believed to be incontinence. However, with the advent of the new terms this is clearly not meaningful for the large number of sufferers who are not incontinent (i.e. OAB Dry patients). Thus, a recent study from Liberman et al [Health Related Quality of Life Among Adults with Symptoms of Overactive Bladder: Results From A US Community-Based Survey; Urology 57(6), 1044-1050, 2001] examined the impact of all OAB symptoms on the quality of life of a community-based sample of the US population. This study demonstrated that individuals suffering from OAB without any demonstrable loss of urine have an impaired quality of life when compared with controls. Additionally, individuals with urgency alone have an impaired quality of life compared with controls.

Thus, urgency is now believed to be the primary symptom of OAB, but to date it has not been evaluated in a quantified way in clinical studies.

It has now been found that darifenacin, and its pharmaceutically acceptable derivatives, is useful in the reduction of urgency in patients suffering from overactive bladder.

This finding is surprising because it could not have been predicted that a compound known to be useful in the treatment of incontinence (i.e. the unwanted and often unconscious leaking of urine) would be able to reduce the feeling of urgency (i.e. the sudden compelling desire to pass urine). It is even more surprising that darifenacin, and its pharmaceutically acceptable derivatives, is able to reduce the feeling of urgency in patients who are not incontinent (i.e. OAB Dry patients).

Thus, according to the present invention, there is provided the use of darifenacin, or a pharmaceutically acceptable derivative thereof, in the manufacture of a medicament for the reduction of urgency in patients suffering from overactive bladder (OAB).

Pharmaceutically acceptable derivatives of darifenacin include solvates and salts, particularly acid addition salts such as the hydrobromide salt.

The patients to be treated may be suffering from wet overactive bladder (OAB Wet) or dry overactive bladder (OAB Dry).

The darifenacin, or a pharmaceutically acceptable derivative thereof, can be administered alone or in any convenient pharmaceutical presentation, including those mentioned in European Patent No 388054. Oral administration is preferred. In the present indication, a suitable dosage of darifenacin, or of the active darifenacin moiety in a pharmaceutically acceptable derivative thereof, for a 70 kg person, is in the range 3.75-40 mg daily, for example 7.5-30 mg daily. The dosage may be administered in, say, 3 divided doses or in a single controlled release formulation.

However, it is preferred that the darifenacin, or a pharmaceutically acceptable derivative thereof, is administered in a dosage form that is adapted to release at least 10% of the darifenacin, or a pharmaceutically acceptable derivative thereof, in the lower gastrointestinal tract of the patient. Such formulations are described in U.S. Pat. No. 6,106,864 (the teaching of which is incorporated herein by reference). The preferred such formulation is a slow release matrix tablet (see particularly Example 3 of U.S. Pat. No. 6,106,864).

The invention further provides darifenacin, or a pharmaceutically acceptable derivative thereof, for use in the reduction of urgency in patients suffering from overactive bladder.

The invention further provides a method of reducing urgency in patients suffering from overactive bladder, which comprises administering darifenacin, or a pharmaceutically acceptable derivative thereof, to a patient in need of such treatment.

The invention is illustrated by the following examples.

EXAMPLES

Clinical Investigations of Urgency in Subjects with Overactive Bladder

Two novel methods for the assessment of urgency were used. The first was for use in a large scale clinical trial, and the second was for use in clinical laboratory studies.

In both of these studies, darifenacin was administered as its hydrobromide salt. It was presented in slow release matrix tablets of the type described in U.S. Pat. No. 6,106,864, particularly Example 3. Tablets were administered once daily (o.d.).

Clinical Study 1

In this study, OAB Wet patients recorded each episode of urgency per day and the overall severity of urgency for each day in a diary. The severity of urgency was recorded by the use of a visual analogue scale (VAS) where the anchor points were mild and severe.

Darifenacin (as hydrobromide salt; 7.5 mg, 15 mg and 30 mg of the active moiety, o.d.) and placebo were evaluated in subjects with a diagnosis of overactive bladder in a multicentre trial and symptoms of urgency were assessed using the VAS at baseline and at the end of the study (12 weeks of treatment).

108 patients (14 male, 94 female) received 7.5 mg; 107 patients (15 male, 92 female) received 15 mg; 114 patients (16 male, 98 female) received 30 mg; and 108 patients (18 male, 90 female) received placebo.

Results

Darifenacin (7.5-30 mg) produced a dose-related reduction in both the number of episodes of urgency and the overall severity of urgency experienced by the OAB subject in the clinical study. The effect was significantly greater than that produced by placebo. The data is presented below in Table 1 and 2.

TABLE 1

Effect of Darifenacin and Placebo on Frequency and Severity of Urgency in OAB Subjects

|  | Placebo | 7.5 mg | 15 mg | 30 mg |
| --- | --- | --- | --- | --- |
| No of episodes of urgency/day |  |  |  |  |
| Baseline | 8.1 | 8.5 | 8.6 | 8.4 |
| Median change from baseline | −1.2 | −1.8 | −2.3* | −3*** |
| Median % Change from baseline | −15.7 | −29.2 | −26.9 | −33.1 |
| Severity of urgency/day |  |  |  |  |
| Baseline | 53.5 | 53.2 | 56.2 | 53.5 |
| Median change from baseline | −3.9 | −7 | −7* | −9.4* |

*P < 0.05,
**P < 0.01,
***P < 0.001

TABLE 2

Effect of Darifenacin on Frequency & Severity of Urgency in OAB subjects corrected for placebo

|  | 7.5 mg | 15 mg | 30 mg |
| --- | --- | --- | --- |
| No of episodes of urgency/day |  |  |  |
| Baseline | 8.5 | 8.6 | 8.4 |
| Median difference from placebo | −0.5 | −1.1* | −1.4*** |
| Severity of urgency/day |  |  |  |
| Baseline | 53.2 | 56.2 | 53.5 |
| Median difference from placebo | −2.5 | −3.8* | −5.5* |

*P < 0.05,
**P < 0.01,
***P < 0.001

Clinical Study 2

This study used a novel method for measuring the time between the first onset of the urgency and the need to micturate, which is known as the 'warning time'. A modified stopwatch was used which required the subject to press a button at the onset of urge and a second button when they felt they needed to micturate.

Darifenacin (as the hydrobromide salt; 30 mg o.d.) and placebo were evaluated in subjects with symptoms of urgency. The subjects were a mixture of OAB Wet and OAB Dry sufferers. The 'warning time' was assessed at baseline and following 2 weeks of treatment using the modified stop watch.

36 patients (29 female, 7 male) received darifenacin; and 36 patients (22 female, 14 male) received placebo.

Results

Treatment with darifenacin of subjects with urgency produced a significant increase in the warning time when compared with subjects treated with placebo. The data are displayed in Table 3.

It should be noted that both OAB Wet and OAB Dry subjects responded to treatment.

TABLE 3

Effect of Darifenacin and Placebo on Warning Time in Subjects with Urgency and Frequency

| Warning Time (Min) | Darifenacin | Placebo |
| --- | --- | --- |
| Baseline (Median) | 4.7 | 9.4 |
| Week 2 (Median) | 8.4** | 4.1 |

*P < 0.05,
**P < 0.01,
***P < 0.001

Median difference from placebo 4.3 minutes

Conclusions

The results show darifenacin produced a clinically significant attenuation of the symptom of urgency in subjects with overactive bladder.

The invention claimed is:

1. A method of reducing urgency in a patient suffering from dry overactive bladder, which comprises administering darifenacin or a pharmaceutically acceptable acid addition salt thereof to the patient suffering from dry overactive bladder.

2. The method of claim 1, wherein the darifenacin is in the form of its hydrobromide salt.

3. The method of claim 1, wherein the darifenacin, or a pharmaceutically acceptable acid addition salt thereof, is administered in a dosage form that is adapted to release at least 10% of the darifenacin, or a pharmaceutically acceptable acid addition salt thereof, in the lower gastrointestinal tract of the patient.

4. The method of claim 3, wherein the dosage form is a slow release matrix tablet.

5. The method of claim 1, wherein the darifenacin, or a pharmaceutically acceptable acid addition salt thereof, is administered in a daily dosage form comprising 3.75 to 40 mg of darifenacin or a pharmaceutically acceptable acid addition salt thereof.

* * * * *

UNITED STATES PATENT AND TRADEMARK OFFICE
CERTIFICATE OF CORRECTION

| | | |
|---|---|---|
| PATENT NO. | : 8,748,476 B2 | Page 1 of 1 |
| APPLICATION NO. | : 12/397433 | |
| DATED | : June 10, 2014 | |
| INVENTOR(S) | : Enrico Colli et al. | |

It is certified that error appears in the above-identified patent and that said Letters Patent is hereby corrected as shown below:

ON THE TITLE PAGE [56] REFERENCES CITED:

Other Publications, under C.R. Chapple, "pp. 3-48," should read --pp. 33-46,--.

IN THE SPECIFICATION:

COLUMN 1:

Line 50, "incontinence" should read --Incontinence--; and
Line 55, "Liberman et al" should read --Liberman et al.--.

COLUMN 2:

Line 10, "is" should read --are--.

COLUMN 3:

Line 19, "Table 1" should read --Tables 1--.

Signed and Sealed this
Ninth Day of December, 2014

Michelle K. Lee
*Deputy Director of the United States Patent and Trademark Office*